United States Patent
Quan

(10) Patent No.: US 10,619,152 B2
(45) Date of Patent: Apr. 14, 2020

(54) ISOLATION OF CELL-FREE NUCLEIC ACIDS FROM BODILY FLUID SAMPLES USING SOLID CHAOTROPIC AGENTS

(71) Applicant: Nancy Quan, Warren, NJ (US)

(72) Inventor: Nancy Quan, Warren, NJ (US)

( * ) Notice: Subject to any disclaimer, the term of this patent is extended or adjusted under 35 U.S.C. 154(b) by 361 days.

(21) Appl. No.: 15/117,569

(22) PCT Filed: Feb. 10, 2015

(86) PCT No.: PCT/US2015/015191
§ 371 (c)(1),
(2) Date: Aug. 9, 2016

(87) PCT Pub. No.: WO2015/120445
PCT Pub. Date: Aug. 13, 2015

(65) Prior Publication Data
US 2016/0369263 A1    Dec. 22, 2016

Related U.S. Application Data

(60) Provisional application No. 61/937,844, filed on Feb. 10, 2014.

(51) Int. Cl.
*C12N 15/10*    (2006.01)
*C12Q 1/6806*    (2018.01)

(52) U.S. Cl.
CPC ....... *C12N 15/1013* (2013.01); *C12Q 1/6806* (2013.01)

(58) Field of Classification Search
CPC .................................................. C12N 15/1013
USPC .......................................... 435/6.1; 536/25.4
See application file for complete search history.

(56) References Cited

U.S. PATENT DOCUMENTS

| 2012/0171675 A1 | 7/2012 | Horlitz et al. | |
|---|---|---|---|
| 2013/0344588 A1* | 12/2013 | Halushka | C12Q 1/6804 435/309.1 |
| 2014/0227712 A1 | 8/2014 | Horlitz et al. | |

FOREIGN PATENT DOCUMENTS

| EP | 3399034 A1 | 5/2017 | |
|---|---|---|---|
| WO | WO20510602 A1 | 11/2005 | |
| WO | WO-2012028880 A1 * | 3/2012 | ......... C12N 15/1013 |

OTHER PUBLICATIONS

AmoyDx® Serum/Plasma cell-free DNA Kit (Spin Column): For purification of DNA from serum or plasma. Amoy Diagnostics Co., LTD. (2013).
Chan et al. "Hypermethylated RASSFIA in Maternal Plasma: A Universal Fetal DNA Marker that Improves the Reliability of Noninvasive Prenatal Diagnosis." Clin. Chem. 52.12(2006):2211-2218.
Chiu et al. "Effects of Blood-Processing Protocols on Fetal and Total DNA Quantification in Maternal Plasma." Clin. Chem. 47.9(2001):1607-1613.
Gahan. "Circulating Nucleic Acids in Plasma and Serum: Diagnosis and Prognosis in Cancer." EPMA J. 1 (2010):503-512.
Kirsch et al. "An Improved Method for the Isolation of Free-Circulating Plasma DNA and Cell-Free DNA from Other Body Fluids." Ann. NY Acad. Sci. 1137(2008):135-139.
Lee. "Agentcourt RNAdvance Blood Kit for Free Circulating DNA and miRNA/RNA Isolation from 2003-300µL of Plasma and Serum." Beckman Coulter Life Sciences. (2015).
Lo et al. "Presence of Fetal DNA in Maternal Plasma and Serum." Lancet. 350(1997):485-487.
Lo et al. "Quantitative Analysis of Fetal DNA in Maternal Plasma and Serum: Implications for Noninvasive Prenatal Diagnosis." Am. J. Hum. Genet. 62(1998):768-775.
Murtaza et al. "Non-Invasive Analysis of Acquired Resistance to Cancer Therapy by Sequencing of Plasma DNA." Nature. 497(2013):108-113.
NextPrep-Mag™ cfDNA Isolation Kit. (For 1-3 mL Plasma Samples) Catalog #3825-01 (16-50 Isolation. Bioo Scientific Corp. (2016).
Swarup et al. "Circulating (Cell-Free) Nucleic Acids—A Promising, Non-Invasive Tool for Early Detection of Several Human Diseases." FEBS Lett. 581(2007):795-799.
White. "Circulating Cell-Free Nucleic Acids: Characteristics, Purification and Applications." Promega Corporation. (2013).
Danagene Circulating DNA Midikit. Danagen-Bioted S.L. (2013).
Quick-cfDNA™ Serum & Plasma Kit, Catalog No. D4076. Zymo Research Corp. (2015).
NucleoSpin® Plasma Xs, Circulating DNA from plasma. Macherey-Nagel. (2014).
GenElute™ Urine Cell-Free DNA Purliciation Mini Kit, Catalog No. DNB300. Sigma-Aldrich. (2015).
MagNA Pure LC Total Nucleic Acid Isloation Kit—Large Volume. Version 17. Roche. (2015).
InviMag® Free Circulating DNA Kit/iG for use on the InviGenius®PLUS. STRATEC Molecular GmbH. (2016).

(Continued)

*Primary Examiner* — Jezia Riley

(74) *Attorney, Agent, or Firm* — Burns & Levinson LLP; Shawn P. Foley

(57) ABSTRACT

Disclosed is a process for isolating cell-free nucleic acid (including both DNA and RNA) or an analog thereof from a bodily fluid, and which entails: a) mixing in a container the bodily fluid, a chaotropic agent in solid form, a detergent and a buffer, and a solid phase which includes magnetic particles, thus forming a reaction mixture containing the cell-free nucleic acid; b) magnetically separating the solid phase having the cell-free nucleic acid bound thereto from the reaction mixture; and optionally c) dissociating the nucleic acid from the solid phase. Compositions and kits are also disclosed.

43 Claims, 3 Drawing Sheets

Specification includes a Sequence Listing.

(56) References Cited

OTHER PUBLICATIONS

Plasma/Serum Cell-Free Circulating DNA Purification Kits, Product Insert, Product # 55500, 55100, 55600, 55800. Norgen Biotek Corporation. (2015).
QIAmp® Circulating Nucleic Acid Handbook. Qiagen. (2011).
MagMAX™ Cell-Free DNA Isloation Kit, User Guide. ThermoFisher Scientific. (2016).
HighPrep™ Cell-Free DNA Kit, Catalog Nos. HPCF-D6, HOCF-D50, HPCF-D100. MagBio Genomics, Inc.
"Easyfficient free-circulating DNA extra." Analytik Jena AG. (2014).
EpiQuik™ Circulating Cell-Free DNA (cfDNA) Isolation Easy Kit. Base Catalog #P-1065. EpiGentek Group Inc. (2016).
Hipro Circulating Cell-Free DNA (cfDNA) Isolation Kit, Catalog # W2603-20, W2603-50. 101Bio.

* cited by examiner

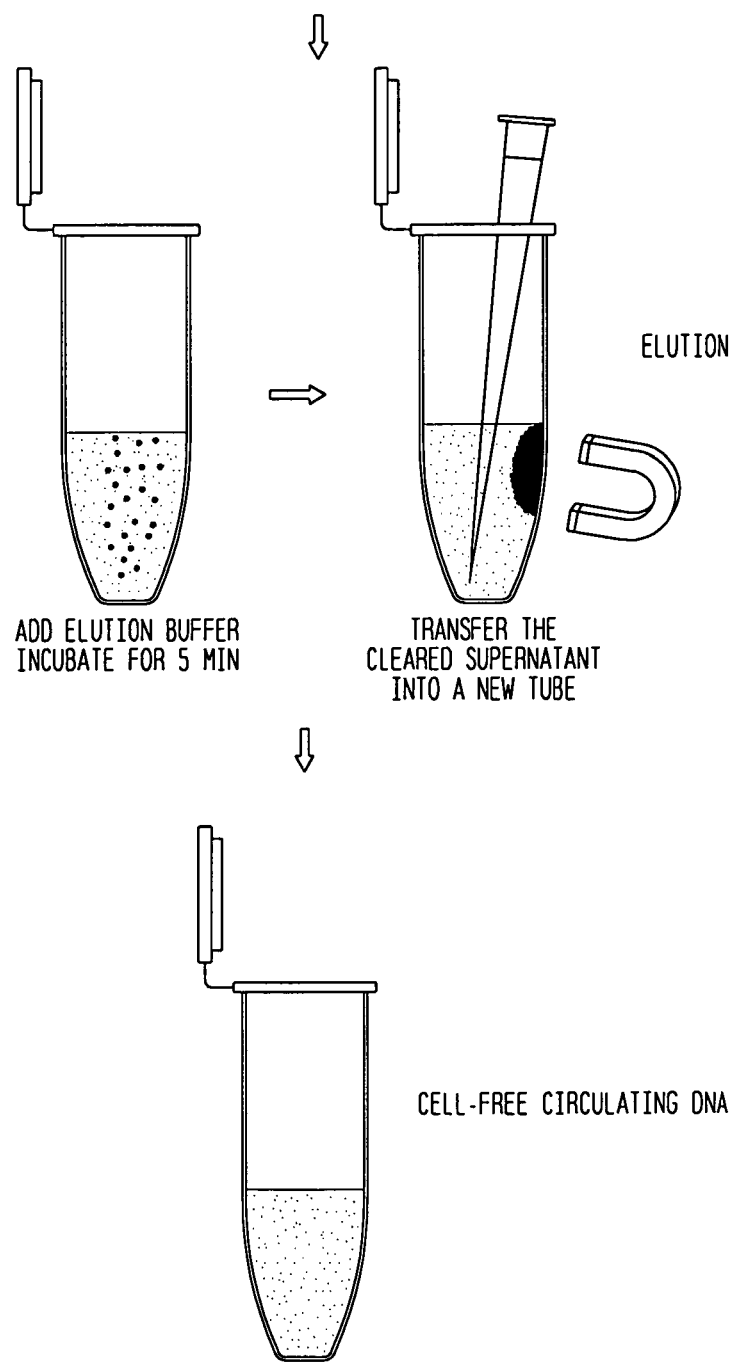
FIG. 2 CON'T

SEQUENCE LISTING

```
<160> NUMBER OF SEQ ID NOS: 4

<210> SEQ ID NO 1
<211> LENGTH: 23
<212> TYPE: DNA
<213> ORGANISM: Homo sapiens

<400> SEQUENCE: 1
tccactttat tccaggcctg tcc                                        23

<210> SEQ ID NO 2
<211> LENGTH: 23
<212> TYPE: DNA
<213> ORGANISM: Homo sapiens
```

```
<400> SEQUENCE: 2
ttgaatggaa tgggaacgaa tgg                                              23

<210> SEQ ID NO 3
<211> LENGTH: 23
<212> TYPE: DNA
<213> ORGANISM: Homo sapiens

<400> SEQUENCE: 3 ccattcctttt gcattccgtt tcc                                             23

<210> SEQ ID NO 4
<211> LENGTH: 23
<212> TYPE: DNA
<213> ORGANISM: Homo sapiens

<400> SEQUENCE: 4
atcgactggc agggaaccaa aag                                              23
```

ISOLATION OF CELL-FREE NUCLEIC ACIDS FROM BODILY FLUID SAMPLES USING SOLID CHAOTROPIC AGENTS

CROSS REFERENCE TO RELATED APPLICATIONS

This application is the U.S. national phase entry under 35 U.S.C. § 371 of International Application No. PCT/US2015/015191, filed Feb. 10, 2015, entitled ISOLATION OF CELL-FREE NUCLEIC ACIDS FROM BODILY FLUID SAMPLES USING SOLID CHAOTROPIC AGENTS, which in turn claims priority to U.S. Provisional Patent Application No. 61/937,844, filed Feb. 10, 2014, the contents of which are incorporated herein by reference in their entirety for all purposes.

BACKGROUND OF THE INVENTION

Circulating cell-free nucleic acid fragments, usually shorter than 1000 bp, such as tumor-specific extracellular nucleic acid fragments in the blood or fetal nucleic acids in maternal blood can be isolated from serum or plasma. (Lo et al., Lancet 350:485-487 (1997); Chan et al., Clin. Chem. 52:2211-2218 (2006)) Analysis of circulating cell-free nucleic acid fragments can be useful in characterizing certain cancers (Murtaza et al., Nature 497(7447):108-12 (2013)) and disease states (Swarup et al., FEBS Lett. 581 (5):795-9 (2007)) as well as in fetal genetic analysis (Lo et al., supra; Chiu et al., Clin. Chem. 47:1607-1613 (2001); Chan et al., supra). The concentrations of circulating cell-free nucleic acid in biological fluids such as plasma, serum, or urine can vary considerably (~50 pg/ml to >100 ng/ml) and depend on the individual, disease state, therapeutic regimen, and period of gestation (Swarup et al., supra). For example, the concentrations of circulating cell-free fetal DNA has been shown to be 3.4% (range 0.39%-11.9%) and 6.2% (range 2.33%-11.4%) of the total plasma DNA in early and late pregnancy, respectively. (Lo et al., Am. J. Hum. Genet. 62(4):768-775 (1998)).

There are a number of known methods of purifying single- and double-stranded NA contained in biological fluids such as human blood, serum, and cultured cells, as well as plants, animal and human tissues, and other specimens. However, such methods can result in very low yields and do not always work well when trying to extract small amounts of nucleic acids from large samples, such as the relatively small amounts of cell-free nucleic acids present in biological fluids. Some methods entail use of chaotropes which facilitate dissociation of cell-free nucleic acid from proteins. As known in the art, higher concentrations of chaotrope are desirable for release of nucleic acids from proteins and capture on a solid phase such as a silicon phase. However, there are disadvantages associated with use of high concentration or molarity of chaotropes. The high molarity of chaotropes may in turn result in viscous solutions which may be difficult to work with. High molarities of chaotropes also necessitate diluting the biological fluid sample several-fold causing undesirably high fluid volumes, which are not amenable for use with existing well established automation equipment. For example, the QIAamp® Circulating Nucleic Acid kit, commercially available from Qiagen, entails about a four-fold dilution of the bodily fluid and use of carrier RNA.

BRIEF SUMMARY OF THE INVENTION

A first aspect of the present invention is directed to a process for isolating cell-free nucleic acid (including both DNA and RNA) or an analog thereof from a bodily fluid. The process or method entails or includes the steps of: a) mixing in a container the bodily fluid, a chaotrope or chaotropic agent in solid form, a detergent and a buffer, and a solid phase that binds nucleic acid, and which includes magnetic particles, thus forming a reaction mixture containing the cell-free nucleic acid; b) magnetically separating the solid phase having the cell-free nucleic acid bound thereto from the reaction mixture; and optionally c) dissociating the nucleic acid from the solid phase. For purposes of the present invention, the terms chaotrope and chaotropic agent are used interchangeably.

In some embodiments the bodily fluid comprises blood or a component thereof, e.g., plasma or serum. In other embodiments, the bodily fluid sample is obtained from a pregnant female, e.g., maternal blood or a component thereof. In other embodiments, the bodily fluid is obtained from a cancer patient who has been treated with a therapeutic agent which is a nucleic-acid analog, e.g., peptide nucleic acid (PNA), a phosphorothioate, locked nucleic acid (LNA), or an oligonucleotide or a chemically modified oligonucleotide. In some embodiments, the chaotropic agent is a guanidinium salt, e.g., guanidinium (iso)thiocyanate. In other embodiments, the chaotropic agent is sodium thiocyanate or urea. In some embodiments, the solid phase includes magnetic particles are coated (e.g., with silica) and have a particle size ranging substantially between about 0.05 and about 1.5 µm and in some embodiments from about 0.05 to about 1.0 µm, and in some embodiments from about 0.1 to about 0.4 µm (e.g., about 0.3 µm).

In some embodiments, the solid phase having cell-free nucleic acid bound thereto is washed at least once with a washing buffer optionally containing a chaotropic agent, and wherein the thus-washed solid phase is washed at least once with an aqueous solution that contains a drying agent, e.g., a monohydric or dihydric alcohol or a polyol, and then dried. In some embodiments, the process or method further entails eluting the thus-dissociated nucleic acid by an aqueous elution buffer.

In some embodiments, the reaction mixture has a volume of about 2 ml to about 10 ml. In some embodiments, the bodily fluid added to form the reaction mixture has a volume of about 2.5 ml to about 5.0 ml.

In contrast to current methodologies in the industry which involve preparation of reaction mixtures using liquid forms of chaotropic agents, the present invention which employs use of chaotropic agents in solid form may be advantageously practiced with relatively small dilution factors, typically ranging from about 1.2 to about 2.0, and in some embodiments from about 1.5 to about 1.8 and in some other embodiments, from about 1.5 to about 1.7, e.g., about 1.6. That is, the dilution factor required by the present invention may be less than half the dilution factor required by current commercial methods such as the QIAamp® Circulating Nucleic Acid kit.

A second aspect of the present invention is directed to a composition useful for separating cell-free nucleic acid from a bodily fluid (wherein the nucleic acid is typically complexed in a proteinaceous matrix) and which includes a chaotropic agent in solid form, a detergent, and a buffer. In some embodiments, the detergent is in solid form; in other embodiments it is liquid. In some embodiments, the buffer is in solid form; in other embodiments it is liquid. Thus, in some embodiments the reagents in the container are all in solid form; and in other embodiments one or two of the reagents are in liquid form. In some embodiments, the chaotropic agent is guanidine thiocyanate, and the detergent is octylphenol ethoxylate. In some embodiments, the composition further includes a solid phase containing magnetic particles.

A third aspect of the present invention is directed to a test kit for isolating cell-free nucleic acid from a bodily fluid, that includes a first container that contains a chaotropic agent in solid form, a detergent, and a buffer. In some embodiments, the chaotropic agent is guanidine thiocyanate, and the detergent is octylphenol ethoxylate. In some embodiments, the chaotropic agent is present in an amount of about 2.0 to about 5.5 grams and wherein the detergent is a liquid and is present in a volume of from about 0.05 to about 0.1 ml. In some embodiments, the kit includes a second container having disposed therein a solid phase including magnetic particles, e.g., magnetic particles coated with silica. In some other embodiments, the solid phase is disposed in the same container as the chaotropic agent and the aqueous detergent composition. In some other embodiments, the test kit further includes an additional container (e.g., a second or third container) having disposed therein a washing buffer optionally containing a drying agent such as a monohydric alcohol, a polyol (e.g., a dihydric alcohol), a ketone or an ether. In some embodiments, the kit further includes another container that contains an elution buffer.

The present invention is believed to provide a solution to a long felt need in the art of diagnostics, and in particular, pre-natal diagnostics. In particular, by proceeding in a direction contrary to the "gold standard" approaches currently employed in the diagnostics industry, the present invention, which employs use of a chaotropic agent in solid form, surprisingly and unexpectedly results in optimal direct capture of cell-free nucleic acid from bodily fluids. More particularly, the use of the chaotropic agent in solid form allows for formation of reaction or test mixtures having high and effective concentrations of the chaotrope, while using minimal volumes of bodily fluid (which is particularly advantageous in the context of pre-natal diagnostics) and minimal sample dilution (e.g., a volume ratio of reaction mixture/bodily fluid that is typically less than 2 and more typically less than 1.6). Further, it does not require use of carrier nucleic acid. These features in turn allow for higher throughput of sample handling, and reduced costs of reagents and disposables.

DETAILED DESCRIPTION

Figure 1:
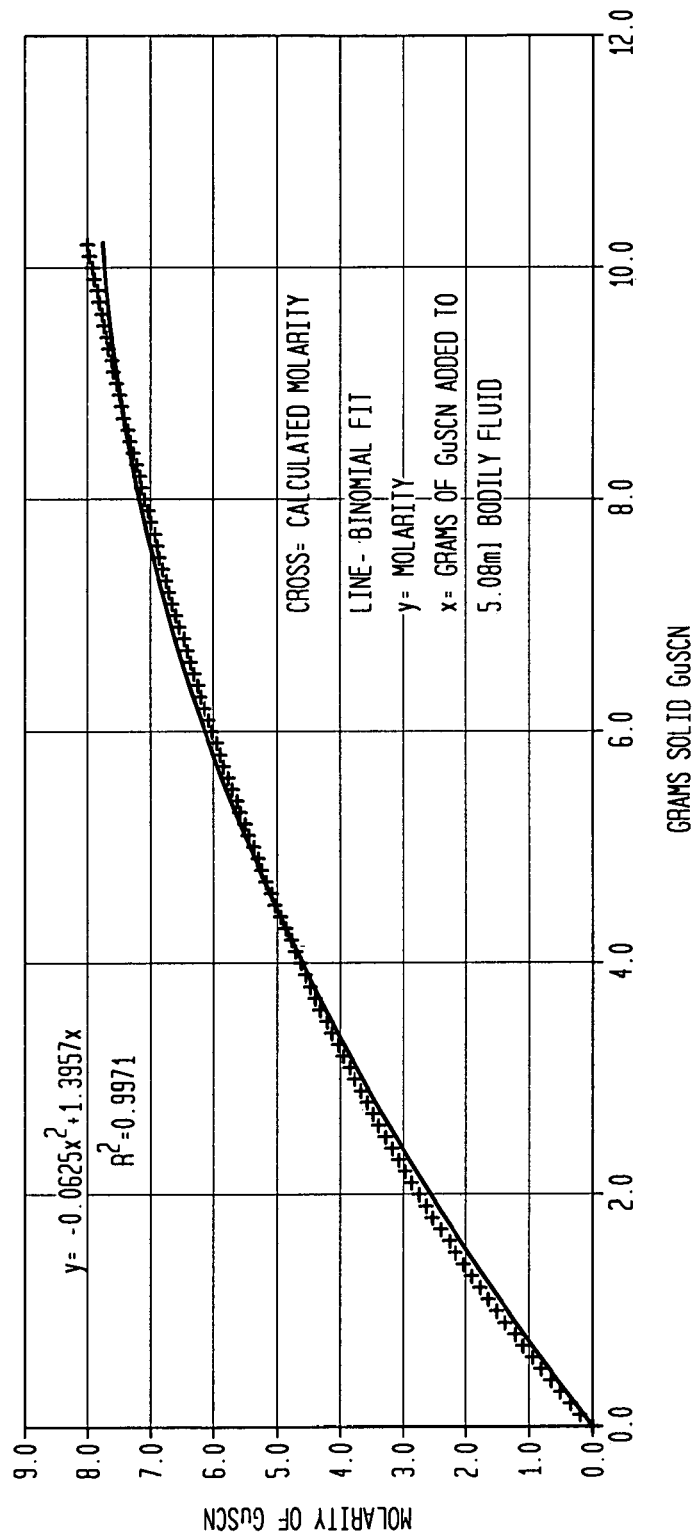
FIG. 1 is a graph that illustrates the relationship between the amount of a solid chaotrope to be used in an embodiment of the present invention to achieve a desired molarity of chaotrope in the final reaction mixture.

The cell-free nucleic acids that may be isolated using the present invention include DNA (single-stranded, double-stranded, covalently closed, and relaxed circular forms), RNA (single-stranded and double-stranded), and nucleic acid analogs such as protein/peptide-nucleic acid (PNA), a phosphorothioate, locked nucleic acid (LNA), and chemically modified oligonucleotides.

The compositions and methods of the present invention may be practiced in connection with a variety of bodily fluids including, for example, plasma, serum, blood, amniotic fluid, aqueous humor, vitreous humor, bile, breast milk, cerebrospinal fluid, cerumen, chyle, chyme, endolymph, paralymph, diarrhea, stool, femal ejaculate, gastric acid, gastric juice, lymph, mucus, pericardial fluid, peritoneal fluid, pleural fluid, purulent exudate, rheum, saliva, cebum, semen, sputum, synovial fluid, lacrimal fluid, sweat, vaginal secretions, vomit, and urine. In some embodiments of the present invention, the bodily fluid is a maternal bodily fluid, such as blood, plasma, or serum. In some embodiments, the bodily fluid sample is blood, plasma, serum or urine.

Depending upon the ultimate uses of the nucleic acid, e.g., the diagnostic test to be performed, the bodily fluid sample may be obtained from healthy or diseased individuals (e.g., cancer patients and stroke patients) and in some embodiments, from pregnant females for purposes of conducting genetic testing to detect for the presence of fetal disease and abnormalities. See, e.g., Lo, et al. (Lancet) supra.; Lo et al. (Am. J. Hum. Gen.) supra.; and Chan et al. supra. In some other embodiments, the fluid sample is taken from a cancer patient who has undergone treatment with an anti-cancer agent that includes a nucleic acid analog such as peptide-nucleic acid (PNA), a phosphorothioate, locked nucleic acid (LNA), and chemically modified oligonucleotides.

Typically, the volume of bodily fluid used in connection with the present invention is from about 2 to about 8 ml, and in some embodiments from about 2.5 to about 5 ml, and yet in other embodiments from about 3 to about 5 ml. In the case of plasma, a particularly preferred volume is about 5 ml.

The chaotrope, detergent and buffer may be conveniently provided as a pre-formed composition, which is combined with the bodily fluid sample to form the reaction mixture. As persons skilled in the art will appreciate, the reaction mixture may be formed by combining the necessary and any other reagents and the bodily fluid sample in any order.

The chaotrope or chaotropic agent used in the compositions and methods of the present invention is in the form of a solid. As persons skilled in the art are aware, many chaotropes are hydroscopic and absorb water. For purposes of the present invention, the term "solid" includes pasty forms of the agent which form as a result of the absorption of water during normal storage conditions. Representative examples of chaotropes that are useful in the present invention include guanidine salts, e.g., guanidine thiocyanate, guanidinium (iso)thiocyanate, and sodium thiocyanate. Other representative chaotropes include iodides (e.g., sodium iodide and potassium iodide) and urea.

The chaotrope is substantially insoluble in the small or negligible volume of the detergent and buffer. It becomes soluble in the reaction mixture, however, once the bodily fluid is present. The amount of solid chaotrope added to form the reaction mixture (or which is present in the composition or kit) is effective to achieve a resultant molarity of the chaotrope typically ranging from about 3 to about 10 M, and in some embodiments from about 4 to about 7.5 M, and in yet other embodiments, from about 5.5 to about 6.5 M. Accordingly, those skilled in the art will be able to determine the amount (in grams) of chaotrope to use, depending upon the volume of the reaction mixture, in accordance with standard techniques.

FIG. 1 is a graph that illustrates the resulting molarity of GuSCN in the reaction mixture (y-axis) as a function of the amount of the grams of the solid chaotrope (x-axis), on the basis of the following equation: $Y=-0.0625X^2+1.3957X$ ($R^2=0.9971$) calculated on the basis of a 5 ml plasma sample and 0.08 ml of 100% TRITON X-100. In general, the amount of the solid chaotrope that is added to form the reaction mixture is from about 2 grams to about 10 grams and in some embodiments, from about 4 gram to about 6 grams. At molarities of about 8 molar or higher, it may be advantageous to incubate the reaction mixture at elevated temperature, such as 60° C. or above.

The detergent may be ionic, including anionic and cationic, non-ionic or zwitterionic. The term "ionic detergent" as used herein includes any detergent which is partly or wholly in ionic form when dissolved in water. Suitable anionic detergents include for example sodium dodecyl sulphate (SDS) or other alkali metal alkylsulphate salts or similar detergents, sarkosyl, or combinations thereof. Suitable nonionic detergents include TERGITOL™ type NP-9 (26-(4-nonylphenoxy)-3,6,9,12,15,18,21,24-octaoxahexacosan-1-ol; available from SIGMA-ALDRICH™, catalog item np9), and TRITON™ X-100 (INCI name: 4-(1,1,3,3-tetramethylbutyl)phenyl-polyethylene glycol or polyethylene glycol p-(1,1,3,3-tetramethylbutyl)-phenyl ether); available from Thermo Scientific, Waltham, Mass., catalog item BP151).

Conveniently, the detergent may be used in a concentration of 0.2 to 30% (w/v), e.g., 0.5 to 30%, preferably 0.5 to 15%, more preferably 1 to 10%. For anionic detergents, concentrations of 1.0 to 5%, e.g., 0.5 to 5%, have been shown to work well. The detergent may be liquid or solid. Liquid detergents may be present in a volume typically ranging from about 0.05 to about 1.5 ml, and in some embodiments from about 0.08 to about 0.5 ml. Solid detergents (e.g., sodium deoxycholate) are typically present in amounts ranging from about 80 to about 500 mg.

The buffer may also be in the form of a liquid (e.g., TRIS HCl, 100 mM, PH8.0, Tris HAc, pH8.0, Tricine HCl, 100 mM) or solid (e.g., phosphate buffer salts, TrisOH/TriHCl solid, TrisHCl/TrisHAc solid). Liquid buffers may be present in a volume typically ranging from about 0.02 to about 0.5 ml, and in some embodiments from about 0.1 ml to about 0.3 ml. Solid buffers are typically present in amounts ranging from about 20 to about 500 mg and in some embodiments from about 50 to about 100 mg.

The reaction mixture may further include a source of monovalent cations, e.g., a salt, to enhance nucleic acid capture on the solid phase. Suitable salts include chloride salts, e.g., sodium chloride, lithium chloride, etc. at concentrations of 0.1 to 1M, e.g., 250 to 500 mM.

The reaction mixture may further include a chelating agent, e.g., EDTA (or a salt thereof), EGTA and other polyamino carboxylic acids conveniently at concentrations of 1 to 50 mM, etc., enzymes, e.g., proteinase K, and reducing agents such as dithiothreitol (DTT) or β-mercaptoethanol, at concentrations of for example 1 to 10 mM.

A preferred combination of detergent, buffer and chelating agent may for example include: 100 mM Tris-HCl pH 7.5, 10 mM EDTA and 1% (v/v) TRITON X-100 (0.08 ml of 100% TRITON, near the critical micelle concentration).

A reaction mixture may then be prepared by mixing the bodily fluid sample, which may or may not be subjected to one or more processing steps such as centrifugation, the solid chaotrope, the buffer, the detergent, and the solid phase containing the magnetic particles. The final volume of the reaction mixture may vary between about 4 and 10 ml, and in some embodiments from about 6 to 9 ml, and in some embodiments from about 7 to about 8 ml. Typical containers in which the reaction mixture may be prepared include 15 ml conical polypropylene, polystyrene, polymethylmethacrylate and similar industry standard tubes with an outer diameter of about 15.8 millimeters. A group of 24 reaction mixtures can be conveniently be prepared in 24 deep-well round bottom blocks with each well having approximately 10 ml volume (e.g., commercially available from Life Technologies™, catalog # CS15124). In some embodiments of the present invention, either before or after preparation of the reaction mixture, the bodily fluid may be subject to one or more pre-processing steps, e.g., centrifugation, so as to remove cellular material therefrom, in which case the supernatant is used for preparing the reaction mixture with the reagents described herein below.

Use of magnetic particles for separating or purifying nucleic acids is well known. The magnetic particle process is increasingly being used as a high-throughput process for the automatic isolation of nucleic acids, in which nucleic acid is isolated from a bodily fluid sample by reversible binding to magnetic particles. The term "magnetic" as used herein means that the solid phase is capable of having a magnetic moment imparted to it when placed in a magnetic field, and thus is displaceable under the action of that field. In other words, a support comprising magnetic particles may be readily removed by magnetic aggregation, which provides a quick, simple and efficient way of separating the particles following the nucleic acid binding, and is a far less painstaking method than traditional techniques such as centrifugation which generate shear forces which may disrupt cells or degrade nucleic acids. Thus, the solid phase with the cell-free nucleic acid associated or complexed thereto may be removed onto a suitable surface by application of a magnetic field, e.g., using a permanent magnet. It is usually sufficient to apply a magnet to the side of the container or vessel (e.g., tube) containing the reaction mixture to aggregate the particles to the wall of the vessel and to pour away or aspirate the remainder of the sample. For purposes of the present invention, the term "magnetic" also embraces "paramagnetic" particles, e.g., superparamagnetic particles such as those described by Sintef in EP-A-106873, as magnetic aggregation and clumping of the particles during reaction can be avoided, thus ensuring uniform nucleic acid extraction.

Magnetic and paramagnetic particles useful for the separation (and eventual purification) of nucleic acid from biological samples are well-known in the art. One such example is magnetic particles of $Fe_3O_4$ (magnetite), e.g., the particles commercially available from Lanxess, under the trade name Bayoxide E. See, e.g., U.S. Pat. No. 8,323,899. Other examples of magnetic particles include MAGAZORB™ paramagnetic particles (available from Promega, Madison, Wis., catalog item MB1001), MAGNESIL™ Blue paramagnetic silica particles (available from Promega, catalog item A2201), and paramagnetic apple or citrus pectin particles. See, U.S. Pat. No. 8,519,119. Yet other magnetic particles, and particularly silica-coated magnetic particles, that may be useful in the practice of the present invention are disclosed in U.S. Pat. No. 5,945,525, as well as those described in Stöber, et al., J. Colloid Interface Science 26(1):62-9 (1968); Zou, et al., Anal. Chem. 80(4):1228-34 (2008); and Xia, et al., Adv. Mater. 12(10):693-713 (2000). Further examples of magnetic particles that may be useful in the practice of the present invention include polyvinyl-alcohol magnetic beads commercially available from Perkin Elmer under the trade name Chemagen, $SiO_2$ and polystyrene magnetic beads commercially available MicroParticles GmbH, $SiO_2$, amine and various other magnetic beads commercially available from Sigma-Aldrich under the trade name TurboBeads, and the magnetic particles sold by Dynal Biotech ASA (Oslo, Norway, previously Dynal AS) under the tradename DYNABEADS.

Once the reaction mixture is prepared, the binding of the nucleic acid to the solid phase may occur over a range of temperatures, typically from about 15 to about 65° C., over a period of time, approximately 10 minutes, up to an hour or so. The reaction mixture may be subjected to shaking or vortexing. The solid phase having the cell-free nucleic acid bound thereto (or complexed therewith) may then be drawn towards the container wall by applying a magnetic field, to facilitate removal of the supernatant (typically by aspirating). After removing the magnetic field, the particles may be re-suspended and washed at least once and preferably several times with a washing buffer that optionally contains a chaotropic agent (which may be the same or different as the chaotrope included in the reaction mixture). In some embodiments, following washing with the washing buffer, the solid phase may be washed yet again, at least once, with a second washing buffer that contains a drying agent (e.g., a monohydric or polyhydric alcohol (or polyol), as well as ketones (e.g., acetone) and ethers).

The cell-free nucleic acid may then be dissociated from the solid phase, e.g., at elevated temperature, such as for example at 60° C. for about 10 minutes, by contacting the solid phase with an elution buffer, e.g., 10 mM Tris HCl or 0.1 mM EDTA. The dissociated cell-free nucleic acid may then be separated from the magnetic particles by re-applying the magnetic field, followed by removal of the eluate (e.g., by pipetting). See, e.g., WO 2003/058649.

Figure 2:
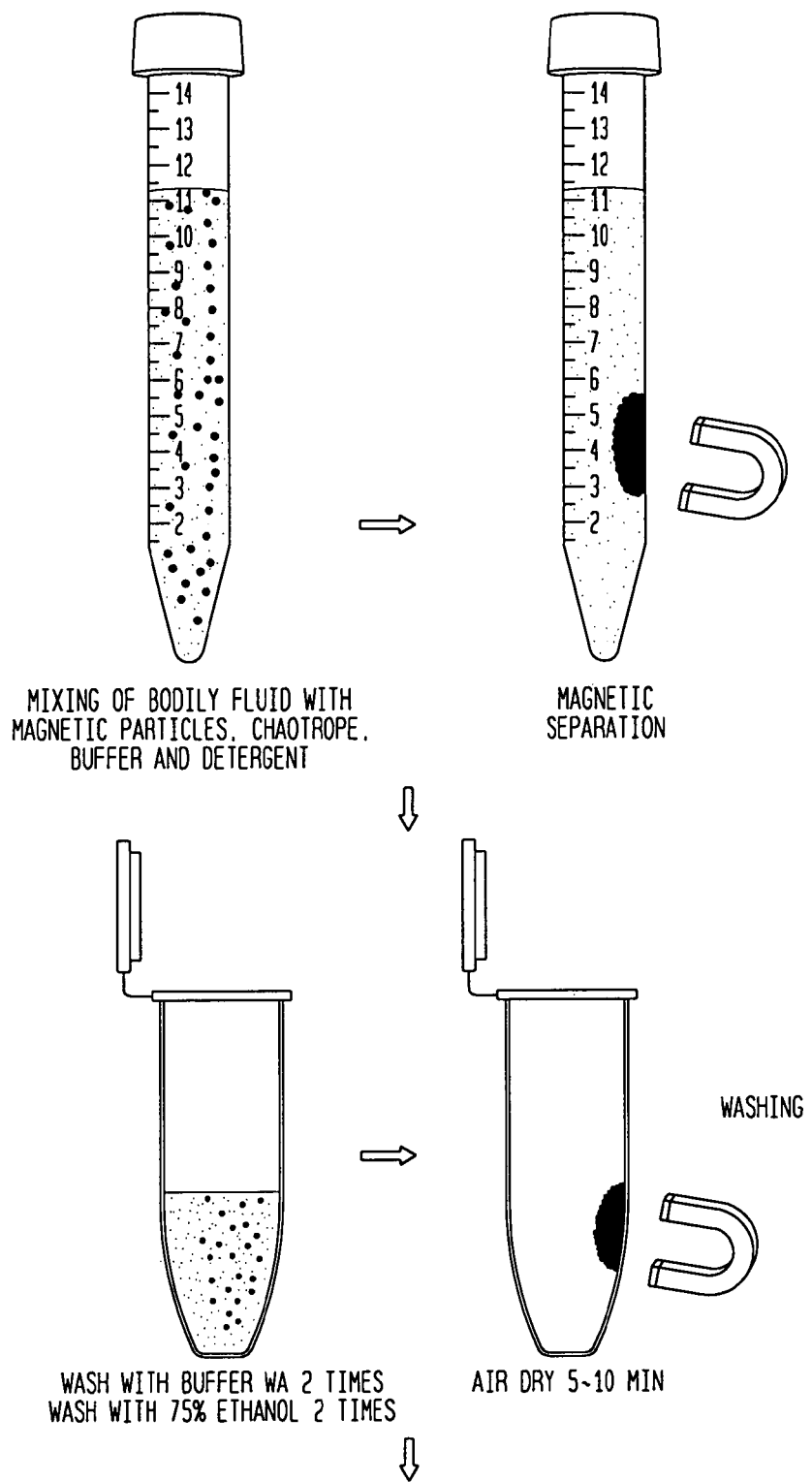
FIG. 2 is a schematic flow diagram of an embodiment of the process of the present invention.

In some embodiments, however, the eluting step may not be required (at least immediately thereafter) in that the solid phase having the cell-free nucleic acid bound thereto can be stored and/or transported for later, downstream use in procedures that may or may not involve eluting the nucleic acid from the solid phase. An embodiment of the present process is schematically illustrated in FIG. 2.

In some embodiments, the cell-free nucleic acid that is dissociated from the solid phase and then eluted may be amplified. A preferred amplification method of target nucleic acid is PCR. The general methods of PCR are well known in the art see, e.g., Innis, et al., *PCR Protocols: A Guide to Methods and Applications*, Academic Press, Inc. N.Y., 1990. PCR reagents and protocols are also available from commercial vendors, such as Roche Molecular Systems. PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available. For example, in the case of quantifying a target mRNA (encoding a protein of interest, e.g., hCG-β, hCRH, hPL, KISS1, TPFI2, PLAC1, or GAPDH) prior to the amplification step, a DNA copy (cDNA) of the mRNA of interest must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in Diagnostic Molecular Biology: Principles and Applications pp. 401-406; Persing et al., eds., Mayo Foundation, Rochester, Minn., 1993; Egger et al., J. Clin. Microbiol. 33:1442-1447 (1995); and U.S. Pat. No. 5,075,212.

Amplification of cell-free nucleic acid may also be accomplished by any other known method, such as ligase chain reaction (LCR), transcription-mediated amplification, and self-sustained sequence replication or nucleic acid sequence-based amplification (NASBA). Further, branched-DNA technology may also be used to quantitatively determine the amount of mRNA in a maternal bodily fluid sample such as blood. See, Nolte, Adv. Clin. Chem. 33:201-235 (1998).

The invention may now be described in accordance with the following non-limiting examples. Unless specified otherwise, all parts are by weight.

EXAMPLES

Example 1) Pregnant women—Image of PCR of highly repetitive region of Y—SRY repeats.
Example 2) Male vs. Female normal—Image of PCR of single copy region of Y.
Example 3) Urine Samples—image of Agilent Bioanalyzer traces.
Compositions and Buffers Used:
Composition (#1) for preparation of Reaction Mixture: for 5 ml of bodily fluid
GuSCN: 5.2 g
Tris: 48.5 mg
EDTA: 58.4 mg
Triton X-100 (100%), 0.08 ml
when added to 5 ml plasma/urine, will make a total volume reaction mixture of 8 ml
Wash buffer (#1):
200 mM NaCl
20 mM Tris HCl, pH8.0
1 mM EDTA
Wash buffer (#2)
Above buffer 50:50 v/v with ethanol resulting 50% v/v wash buffer solution
Elution Buffer
1 mM Tris-HCl pH 8.0
0.1 mM EDTA
Common Protocol Features:
Purification Protocol:
Sample volumes were ~5 ml. For samples less than 5 ml (as indicated), volume was adjusted to 5 ml with phosphate buffered normal saline.
Blood samples were collected using K-EDTA (Lavender top) BD Vacutainer™ tubes. Samples were spun at ~2500×g for 7 minutes within 20 minutes of collection (room temperature). The supernatant, plasma, 5 ml (or as indicated) was used for processing.
Urine samples were collected in sterile urine collection cups and spun at ~2500×g (for cell-free DNA) or used directly as indicated in the example.
Procedure:
The appropriate amount of plasma or urine was added to the tube containing the composition (#1) and mixed thoroughly for approximately 10 minutes at room temperature via inversion.
Fully resuspended NGS Beads™ (via vortexing for 1 minute) were added via pipetting 30 µl of magnetic beads to the bodily fluid and the composition, thus preparing the reaction mixture. Complete mixing of the magnetic beads was ensured by vortexing for 1 minute. The reaction mixtures were incubated at room temperature for 10 minutes. The tubes were mixed by inverting every 2-3 minutes during incubation.
Reaction mixtures were placed onto a magnetic stand for at least 1 minute. The cleared supernatant was aspirated and discarded.
The samples were removed from the magnetic stand and 600 µl of Buffer WA (diluted 1:1 with absolute ethanol before use) was added and used to resuspend the magnetic beads by vortexing for 30 seconds. The resuspended beads were transferred to a 1.5 ml conical microcentrifuge tube.

Samples were placed onto a magnetic stand for at least 1 minute. The cleared supernatant was aspirated and discarded.

The samples were removed from the magnetic stand and 600 μl of Buffer WA (dilute 1:1 with absolute ethanol before use) was added and used to resuspend the magnetic beads by vortexing for 30 seconds.

Samples were placed onto a magnetic stand for at least 1 minute. The cleared supernatant was aspirated and discarded.

The samples were removed from the magnet stand and the magnetic beads resuspended in 600 ul of 75% v/v ethanol in water.

Samples were placed onto a magnetic stand for at least 1 minute. The cleared supernatant was aspirated and discarded.

The samples were removed from the magnet stand and the magnetic beads resuspended in 600 ul of 75% v/v ethanol in water.

Samples were placed onto a magnetic stand for at least 1 minute. The cleared supernatant was aspirated and discarded.

The magnetic beads were air-dried at room temperature for 10 minutes.

50 μl elution buffer (10 mM Tris-HCl, pH8.0, 0.1 mM EDTA) was added, and the magnetic beads resuspended and incubated at room temperature for 5 minutes.

The samples were placed on the magnetic stand for 1 minute and the cleared supernatant containing the purified circulating cell-free DNA was transferred to a microfuge tube for long term storage (−20° C.) and further analysis as indicated in the examples.

Example 1) Pregnant Women—Image of PCR of Highly Repetitive Region of Y—SRY Repeats PCR Primers:

```
Sequence 1:
                                       (SEQ ID NO: 1)
5'-TCCACTTTATTCCAGGCCTGTCC-3'

Sequence 2:
                                       (SEQ ID NO: 2)
5'-TTGAATGGAATGGGAACGAATGG-3'
```

Standard PCR Conditions:
5 ul of 50 ul PCR reaction loaded onto gel for analysis
1% Agarose TBE gel analysis of PCR products Lane Designation:
1 & 12 MW Markers
2-9) 7 week pregnant women 2,4,9=male fetuses
10 Male control plasma
11 Female control—non-pregnant Example 2 Male vs. Female Lane 1=MW marker
Lanes 2 & 6=male controls
All other lanes Female
PCR Primers—single copy on Y chromosome

```
Primer 3:
                                       (SEQ ID NO: 3)
5'-CCA TTC CTT TGC ATT CCG TTT CC-3'

Primer 4:
                                       (SEQ ID NO: 4)
5'-ATC GAC TGG CAG GGA ACC AAA AG-3'
```

Example 3) Urine Samples—Image of Agilent Bioanalyzer Traces 5 ul of 50 ul of eluted sample loaded. Agilent DNA Bioanalyzer
9=no DNA
10=cell-free DNA (urine sample spun)
11=sample not spun—note presence of high molecular weight DNA All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A process for isolating cell-free nucleic acid or an analog thereof from a bodily fluid, comprising: a) mixing in a container the bodily fluid, a chaotropic agent in solid form, a detergent in solid form and a buffer in solid form, and a solid phase which comprises magnetic particles, thus forming a reaction mixture containing the cell-free nucleic acid, wherein the reaction mixture has a volume of about 2 ml to about 10 ml, and wherein the chaotropic agent is present in the reaction mixture in an amount of about 2 to about 10 grams and at a concentration of about 3M to about 10M; b) magnetically separating the solid phase having the cell-free nucleic acid bound thereto from the reaction mixture; and optionally c) dissociating the nucleic acid from the solid phase.

2. A process according to claim 1, wherein the bodily fluid comprises blood or a component thereof.

3. A process according to claim 2, wherein the blood component is plasma.

4. A process according to claim 2, wherein the blood component is serum.

5. A process according to claim 1, wherein the bodily fluid comprises urine.

6. A process according to claim 1, wherein the bodily fluid sample is obtained from a pregnant female.

7. A process according to claim 6, wherein the bodily fluid is maternal blood or a component thereof.

8. A process according to claim 1, wherein the bodily fluid is obtained from a cancer patient who has been treated with a therapeutic agent which comprises a nucleic-acid analog.

9. A process according to claim 8, wherein the nucleic acid analog is a peptide nucleic acid (PNA), a phosphorothioate, locked nucleic acid (LNA), or an oligonucleotide or a chemically modified oligonucleotide.

10. A process according to claim 1, wherein the chaotropic agent is selected from the group consisting of a guanidinium salt, an iodide, sodium thiocyanate and urea.

11. A process according to claim 10, wherein the guanidinium salt is guanidinium (iso)thiocyanate.

12. A process according to claim 1, wherein the nucleic acid is DNA.

13. A process according to claim 1, wherein the nucleic acid is RNA.

14. A process according to claim 1, wherein the solid phase further comprises silica particles having a particle size ranging substantially between 0.05 and 0.4 µm.

15. A process according to claim 1, further comprising washing the solid phase having the cell-free nucleic acid bound thereto with a washing buffer optionally containing a chaotropic agent.

16. A process according to claim 15, further comprising washing the thus-washed solid phase with an aqueous solution comprising a monohydric alcohol or a polyol.

17. A process according to claim 16, wherein the nucleic acid is dissociated from the solid phase by an aqueous elution buffer.

18. A process according to claim 1, wherein the reaction mixture has a volume of about 2 ml to about 10 ml.

19. A composition useful for isolating cell-free nucleic acid from a bodily fluid, comprising a chaotropic agent in solid form, a buffer in solid form, and a detergent in solid form, wherein the chaotropic agent is present in an amount of about 2 to about 10 grams and is selected such that when mixed with a volume of sample fluid to form a reaction mixture having a volume of about 2 to about 10 milliliters, the chaotropic agent is present in a concentration of about 3M to about 10M.

20. A composition according to claim 19, wherein the buffer is TRIS HCl.

21. A composition according to claim 19, wherein the detergent is sodium deoxycholate.

22. A composition according to claim 19, wherein the detergent is sodium dodecyl sulfate (SDS).

23. A composition according to claim 19, further comprising magnetic particles.

24. A composition according to claim 19, further comprising a chelating agent or an anti-clotting agent, or a combination thereof.

25. A test kit for isolating cell-free nucleic acid from a bodily fluid, comprising in a first container, a chaotropic agent in solid form in an amount of about 2 to about 10 grams and is selected such that when mixed with a volume of sample fluid to form a reaction mixture having a volume of about 2 to about 10 milliliters, the chaotropic agent is present in a concentration of about 3M to about 10M, a buffer in solid form, and a detergent in solid form.

26. A test kit according to claim 25, wherein the chaotropic agent is guanidine thiocyanate, and the detergent is SDS.

27. A test kit according to claim 25, wherein the first container further comprises a solid phase comprising magnetic particles.

28. A test kit according to claim 25, further comprising a second container having disposed therein a solid phase comprising magnetic particles.

29. A test kit according to claim 27, wherein the magnetic particles are coated with silica.

30. A test kit according to claim 25, further comprising a second container having disposed therein a washing buffer comprising a chaotrope.

31. A test kit according to claim 25, further comprising a third container comprising a washing buffer comprising a drying agent.

32. A test kit according to claim 25, further comprising a fourth container comprising an elution buffer.

33. A test kit according to claim 25, comprising a first container having disposed therein the chaotrope in solid form in an amount of about 2 to about 10 grams and is selected such that when mixed with a volume of sample fluid to form a reaction mixture having a volume of about 2 to about 10 milliliters, the chaotropic agent is present in a concentration of about 3M to about 10M, the solid buffer and the solid detergent; a second container having disposed therein a solid phase comprising magnetic particles coated with silica; and a third container comprising a washing buffer comprising ethanol.

34. A test kit according to claim 28, wherein the magnetic particles are coated with silica.

35. A composition according to claim 19, wherein the chaotropic agent is present in an amount of about 4 to about 6 grams.

36. A test kit according to claim 25, wherein the chaotropic agent is present in an amount of about 4 to about 6 grams.

37. A composition according to claim 19, wherein the chaotropic agent is present in an amount effective to achieve a molarity of about 4M to about 6M when mixed with a volume of sample fluid of about 2 to about 10 milliliters.

38. A composition according to claim 19, wherein the chaotropic agent is present in an amount effective to achieve a molarity of about 4M to about 7.5M when mixed with a volume of sample fluid of about 2 to about 10 milliliters.

39. A composition according to claim 19, wherein the chaotropic agent is present in an amount effective to achieve a molarity of about 5.5M to about 6.5M when mixed with a volume of sample fluid of about 2 to about 10 milliliters.

40. A composition according to claim 19, wherein the chaotropic agent is present in an amount effective to achieve a molarity of about 3M to about 10M when mixed with a volume of sample fluid of about 2.5 to about 5 milliliters.

41. A composition according to claim 19, wherein the chaotropic agent is present in an amount effective to achieve a molarity of about 3M to about 10M when mixed with a volume of sample fluid of about 3 to about 5 milliliters.

42. A composition according to claim 19, wherein the chaotropic agent is present in an amount effective to achieve a molarity of about 3M to about 10M when mixed with a volume of sample fluid of about 5 milliliters.

43. A composition according to claim 19, wherein the chaotropic agent is present in an amount effective to achieve a molarity of about 5.5M to about 6.5M when mixed with a volume of sample fluid of about 3 to about 5 milliliters.

* * * * *